United States Patent [19]

Mitchell et al.

[11] 4,122,164

[45] Oct. 24, 1978

[54] DENTAL CREAM COMPOSITION

[75] Inventors: Robert Lee Mitchell, Somerset; William John Chung, Spotswood, both of N.J.

[73] Assignee: Colgate-Palmolive Company, New York, N.Y.

[21] Appl. No.: 824,996

[22] Filed: Aug. 15, 1977

Related U.S. Application Data

[60] Division of Ser. No. 618,855, Oct. 2, 1975, Pat. No. 4,075,317, which is a continuation-in-part of Ser. No. 464,898, Apr. 29, 1974, abandoned, which is a continuation-in-part of Ser. No. 369,730, Jun. 13, 1973, abandoned.

[51] Int. Cl.$^2$ .......................... A61K 7/16; A61K 7/18; B65D 85/14; B65D 81/26
[52] U.S. Cl. ...................................... 424/52; 206/277; 206/524.4; 424/49; 424/57
[58] Field of Search .................................. 424/49–58; 206/277, 524.4

[56] References Cited

U.S. PATENT DOCUMENTS

| | | | |
|---|---|---|---|
| 2,191,199 | 2/1940 | Hall | 424/57 |
| 2,941,926 | 6/1960 | Salzmann et al. | 424/57 |
| 3,227,617 | 1/1966 | Manminn et al. | 424/52 |
| 3,227,618 | 1/1966 | Manminn et al. | 424/52 |
| 3,624,199 | 11/1971 | Norfleet | 424/57 |
| 3,634,585 | 1/1972 | Manahan et al. | 424/52 |
| 3,662,060 | 5/1972 | Clippondale et al. | 424/57 |
| 3,678,155 | 7/1972 | Clippondale et al. | 424/52 |
| 3,822,345 | 7/1974 | Murray et al. | 424/52 |
| 3,864,471 | 2/1975 | King et al. | 424/52 |
| 3,935,304 | 1/1976 | Januszewski et al. | 424/49 |
| 3,941,877 | 3/1976 | King et al. | 424/52 |
| 4,034,076 | 7/1977 | Coulson et al. | 424/49 |

FOREIGN PATENT DOCUMENTS

| | | | |
|---|---|---|---|
| 1,066,412 | 6/1957 | France | 424/57 |
| 777,556 | 6/1957 | United Kingdom | 424/52 |
| 1,132,830 | 11/1968 | United Kingdom | 424/52 |

OTHER PUBLICATIONS

Degussa Technical Bulletin #49 "Aerosil" in Pharmaceuticals and Cosmetics Degussa Pigments Division p. 29 reprinted from drugs made in Germany vol. 13, pp. 47–58, No. 717 (1970).

Van Wazir "Phosphorus and its Compounds" (1961) vol. II, pp. 1652–1653, vol. I pp. 630–659, 665–678, 775–777 Interscience Publishers, Inc. N.Y. N.Y.

Primary Examiner—Shep K. Rose
Attorney, Agent, or Firm—Robert L. Stone; Murray M. Grill; Herbert S. Sylvester

[57] ABSTRACT

Dental cream suitable for use in an unlined aluminum container comprising between about 35% and 60% of abrasive containing alumina as the major abrasive component and as agents to render the dental cream compatible with an unlined aluminum container, calcium carbonate present as minor abrasive component in amount of at least about 1% of the dental cream and a dissolved or dispersed silicate present in amount of about 0.05%–0.25%. The composition also desirably contains a water-soluble monofluorophosphate salt in amount which provides 0.01–1% fluoride in the dental cream and when the dental cream contains the monofluorophosphate salt and more than about 5% calcium carbonate, an alkali metal tripolyphosphate in an amount up to about 1.5% is also present.

10 Claims, No Drawings

DENTAL CREAM COMPOSITION

This application is a divisional of application Ser. No. 618,855, filed Oct. 2, 1975, now U.S. Pat. No. 4,075,317, issued Feb. 21, 1978, which is a continuation-in-part of Ser. No. 464,898, filed Apr. 29, 1947 now abandoned, which is a continuation-in-part of Ser. No. 369,730, filed June 13, 1973, now abandoned.

This invention relates to a dental cream composition suitable for use in an unlined aluminum tube. The composition contains alumina as the major abrasive component.

It has been discovered that alumina-containing dental creams have desirable characteristics. However, it has been difficult to formulate dental creams containing substantial amounts of alumina which can be compatibly packaged in unlined aluminum tubes. The alumina appears to adversely affect the stability of the dental cream, particularly in such tubes.

The packaging of dental creams in unlined aluminum tubes is desired in view of the relatively low cost of such tubes and of their light weight. When dental creams are packaged in unlined aluminum containers, it is sometimes found that the containers corrode and/or dental cream formulations become unstable. This is particularly evident when the dental creams contain alumina and also when they further contain a water-soluble monofluorophosphate salt.

The present invention provides a stable dental cream composition containing alumina, which also desirably may contain a water-soluble monofluorophosphate salt.

The present invention provides a dental cream composition suitable for use in, and compatable with, an unlined aluminum container comprising a dental cream vehicle having dispersed or dissolved therein about 35% and 60%, abrasive which abrasive consists essentially of alumina and calcium carbonate, the alumina being present in excess of said calcium carbonate, said calcium carbonate being in amount of at least about 1% of the total dental cream and between about 0.05% and 0.25% of a dissolved or dispersed silicate.

The dental cream may also desirably contain a water-soluble monofluorophosphate salt in an amount which provides between about 0.01% and 1% of fluoride in the dental cream and when the monofluorophosphate salt is present and the amount of calcium carbonate is more than 5% of the dental cream, an alkali metal tripolyphosphate is present in an amount up to about 1.5%.

The inclusion of both calcium carbonate as the minor abrasive component, but in amount of at least about 1% of the dental cream and of about 0.05 – 0.25% of the dissolved or dispersed silicate is necessary in order to render the dental cream containing alumina as the major abrasive component compatible with an unlined aluminum container. It is preferred that the dental cream contain at least about 2% of calcium carbonate. Furthermore, the inclusion in the dental cream composition of calcium carbonate in an amount of at least about 1% acts to stabilize the composition with consequent retention of active fluoride. Dental cream compositions containing at least about 4%, e.g., between 4% and 5%, calcium carbonate have added effectiveness in connection with stain removal from teeth. Dental creams containing larger amounts of calcium carbonate (above 5%), up to a maximum of less than the amount of alumina, retain the specified advantages.

It is preferred that the abrasive consist essentially of between about 4% and 5% calcium carbonate and the remainder alumina.

Although the total amount of abrasive in the dental cream composition may be within the broad range of about 35%–60%, it is preferred that it be within the range of about 40%–52%. When larger amounts of abrasive are included in the composition, e.g., above about 54%, the composition tends to become unduly thick. Similarly, compositions containing less than 40% abrasive tend to be too thin. The compositions containing the abrasive within the preferred range also preferably contain the preferred concentration of a gum. Increased amounts of gum tend to thicken the composition and decreased amounts tend to make it less thick. When amounts of abrasive are used outside the aforesaid preferred range, the consistency of the composition may be adjusted by a compensating change in the amount of gum.

The dental cream containing monofluorophosphate salt and more than about 5% calcium carbonate also contains an alkali metal (e.g. sodium or potassium) tripolyphosphate typically in an amount between about 0.05% and 1.5%, and preferably between about 0.15% and 1% to improve the ability of the dental cream to retain monofluorophosphate as fluoride. The preferred alkali metal tripolyphosphate is sodium tripolyphosphate ($Na_5P_3O_{10}$). The amount of the tripolyphosphate is preferably increased with increased calcium carbonate. The preferred addition of the tripolyphosphate is about 0.2% with relatively high calcium carbonate content, e.g., 20% of the dental cream. The addition of between 0.2%–0.7% is preferred. Larger amounts than about 1.5% tend to unduly thicken the dental cream. Less than about 0.05% of the tripolyphosphate is generally considered inconsequential.

Calcium carbonate in the form of chalk may be used. Chalk in the form of a powder having a particle size of between about 1 and 10 microns is preferred. It is also preferred to use a grade of calcium carbonate of relatively high apparent specific gravity, e.g., about 0.9 to 1.2. If desired, calcium carbonate grades of lower apparent specific gravity, e.g., 0.7 to 0.9 may be used. "Apparent specific gravity" refers to the untamped specific gravity of the calcium carbonate. Calcium carbonate containing even small quantities of magnesium carbonate, e.g., about 0.1–0.3%, tends to adversely affect the stability of the dental cream with consequent loss of active fluoride. The stable dental creams of the present invention tolerate small amounts of impurity, e.g., magnesium carbonate in amounts less than about 1%. However, it is preferred that the magnesium carbonate should be about 0.1%–0.5% based on the calcium carbonate.

The alumina employed in accordance with the instant invention is small in particle size, i.e., at least about 85% of the particles are smaller than 20 microns and is preferably hydrated, such as that classified as Gibbsite (alpha alumina trihydrate) and normally represented chemically as $Al_2O_3 \cdot 3H_2O$ or $Al(OH)_3$. The average particle size of Gibbsite is generally 6 to 9 microns with the following particle size distribution:

<30 mirons: 94–99%
<20 microns: 85–93%
<10 microns: 56–67%
< 5 microns: 28–40%

Other types of alumina which may be employed in accordance with the instant invention include kappa type alumina, gamma phase alumina, beta phase alumina and mixtures thereof with alpha alumina trihydrate. Microcrystalline alumina having a mean particle size of as little as 0.3 micron or less with 90–95% of the particles being smaller than 0.5 micron may also be used. The alpha alumina trihydrate sold by Alcoa as C333 is a fine grade of Gibbsite and is particularly highly desirable. The average particle size of C333 alumina is about 2.5–8.5 microns. It is obtained by fine grinding of the grade of alumina trihydrate sold by Alcoa as C33.

Dental creams, and particularly those containing the preferred hydrated alumina, may contain a small amount, e.g., up to about 2% and preferably 0.7–1%, of a harder abrasive to enhance the polishing function of the dental cream. Useful polishing abrasives include calcined aluminum oxide and zirconium silicate.

When water soluble monofluorophosphate is included in the composition it is present in an amount to provide between about 0.01% and 1% (preferably about 0.04% – 0.1%) fluoride. It is preferably an alkali metal monofluorophosphate such as sodium monofluorophosphate, lithium monofluorophosphate, potassium monofluorophosphate and ammonium monofluorophosphate. The preferred salt is sodium monofluorophosphate, $Na_2PO_3F$, which as commercially available, may vary considerably in purity. It may be used in any suitable purity provided that any impurities do not substantially adversely affect the desired properties. In general, the purity is desirable at least about 80%. For best results, it should be at least 85%, and preferably at least 90% by weight of sodium monofluorophosphate with the balance being primarily impurities or by-products of manufacture such as sodium fluoride, water-soluble sodium phosphate salt, and the like. Expressed in another way, the sodium monofluorophosphate employed should have a total fluoride content of above 12%, preferably above 12.7%, a content of not more than 1.5%, preferably not more than 1.2% of free sodium fluoride; and a sodium monofluorophosphate content of at least 12%, preferably at least 12.1%, all calculated as fluorine.

Other monofluorophosphate salts which have sufficient water solubility for use in the instant invention include calcium monofluorophosphate, magnesium monofluorophosphate and aluminum monofluorophosphate. In accordance with this invention, the term "monofluorophosphate" also includes monofluoropolyphosphates such as $Na_4P_3O_9F$, $K_4P_3O_9F$, $(NH_4)_4P_3O_9F$, $Na_3kP_3O_9F$, $(NH_4)_3NaP_3O_9F$ and $Li_4P_3O_9H$.

Typically, the monofluorophosphate is present in amount which provides about 0.01–1% fluorine to the dentifrice. Thus, sodium monofluorophosphate is present, typically, in amount of about 0.076% to about 7.6%.

The dental cream includes an alkali metal silicate, which together with the calcium carbonate provide stability for the dental cream in which the major portion of the abrasive is alumina in an unlined aluminum container. The preferred alkali metal silicate is sodium silicate, e.g., a hydrated sodium silicate in flake form containing $Na_2O.SiO_2.H_2O$ in a ratio of about 1:2–3.2:5. The silicate may also be obtained in an aqueous solution, e.g., 40% solids, and also may be formed in situ in the dental cream by adding precursors thereof. Silica in the form of very fine particles, e.g., fumed silica, which forms dispersions, e.g., of colloidal size, may be used instead of the preferred silicate.

The dental cream compositions contain the silicate, when calculated as sodium silicate in an amount between about 0.05% and 0.25% (preferably 0.15% – 0.25%) with 0.18% to about 0.2% being especially preferred.

Suitable surface active or detersive material may be included in the dentifrice compositions. Such compatible materials are desirable to provide additional detersive, foaming and antibacterial properties depending upon the specific type of surface active material and are selected similarly. These detergents are water-soluble organic compounds usually, and may be anionic, nonionic or cationic in structure. It is preferred to use the water-soluble non-soap or synthetic organic detergents usually. Suitable detersive materials are known and include, for example, the water-soluble salts or higher fatty acid monoglyceride monosulfate detergent (e.g., sodium coconut fatty acid monoglyceride monosulfate), higher alkyl sulfate (e.g., sodium lauryl sulfate), alkyl aryl sulfonate (e.g., sodium dodecyl benzene sulfonate) higher fatty acid esters of 1,2-dihydroxy propane sulfonate (e.g., sodium coconut fatty acid ester of 1,2-dihydroxy propane sulfonate) and the like.

The various surface active materials may be used in any suitable amount, generally from about 0.05 to about 10% by weight, and preferably from about 0.5 to 5% by weight of the dentifrice composition, with about 1.5 to 2% especially preferred.

The dental cream composition may also contain at least one of the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxlyic acids having about 2 to 6 carbons, usually the monocarboxylic acid compounds. Suitable compounds are the fatty acid amides of glycine, sarcosine, alanine, 3-amino-propanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compound," "sarcoside," and the like refers to such compounds having a free carboxylic group or the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of the said amide material.

The liquids and solids forming the dental cream composition should be proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a binder or humectant such as glycerine and/or sorbitol. It is preferred to use glycerine or mixtures of a major portion of glycerine with a minor portion of sorbitol. The humectant is generally used in an amount between 20% and 25%, and preferably about 22%. The total liquid content will generally be about 20-65% by weight of the formulation, with water being in an amount to bring the total of components to 100%.

It is preferred to use also a gelling agent in dental creams such as the natural and synthetic gum and gum-like material, e.g., Irish moss, gum tragacanth, sodium carboxymethylcellylose, polyvinylpyrrolidone, starch and the like; all being referred to as "gum". The Irish moss and sodium carboxymethylcellylose are compatible particularly and are preferred gelling agents. The gum content is usually in an amount up to about 10% and preferably about 0.5-5% by weight of the formulation, with gum in an amount of about 0.9% – 1.3% especially preferred.

The total of liquid and gelling agent (gum) form the dental cream vehicle in which the other components are dispersed or dissolved.

Various other materials may be incorporated in the dental creams of this invention. Examples thereof are coloring or whitening agents, preservatives, silicones, chlorophyll compounds and ammoniated materials such as urea, diammoniumphosphate and mixtures thereof. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidehexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;

and their non-toxic acid addition salts.

Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the instant invention.

The dental cream should have a pH practical for use. The range is preferably alkaline and may range up to about 9.9. The dental creams containing the preferred amounts of the preferred components typically have a pH range between about 9 and 9.2, e.g., about 9.02-9.03. The reference to the pH is meant to be the pH determination directly on the dental cream.

The instant dental cream compositions are highly efficacious in use. They exhibit desirable cosmetic and rheological properties and may be stored and dispensed from conventional style collapsible unlined aluminum tubes. They also exhibit unusually desirable flavor characteristics.

The dental cream compositions may be prepared by conventional manufacturing methods, as disclosed in Chapter XV of Sagarin's *Cosmetics, Science & Technology* (1957) Interscience Publishers, Inc.

The following specific examples are further illustrative of the nature of the present invention, but it is to be understood that the invention is not limited thereto. All percentages and amounts of the various ingredients in the specification are by weight based on the total dental cream composition unless otherwise specified. The dental cream compositions of this invention are prepared in the conventional manner, namely by admixing solid and liquid components with the gum and mixing until swelling occurs with the formation of a gel, and then adding the abrasives and forming a homogeneous mixture.

In the process of preparing the dental cream compositions it is noteworthy that calcium carbonate in amount of at least about 2% of the dental cream up to an amount less than the amount of alumina is dispersed in the dental vehicle and the silicate in amount of about 0.05%-0.25% is dispersed or dissolved in the dental vehicle in order to provide dental cream compositions which are compatible with and stable in unlined aluminum containers.

EXAMPLE 1

|  | % |
|---|---|
| hydrated alumina | 46.25 |
| calcium carbonate (chalk) | 5 |
| sodium silicate | 0.2 |
| glycerine | 22 |
| sodium benzoate | 0.5 |
| sodium saccharin | 0.2 |
| sodium carboxymethyl cellulose | 1.1 |
| sodium monofluorophosphate | 0.76 |
| detergent | 2 |
| flavor | 0.9 |
| water (to make up 100%) |  |

The monofluorophosphate provides 0.1% of fluoride in the dental cream. The dental cream was packaged in an unlined aluminum tube and aged at an elevated temperature in an accelerated aging test. The composition is stable, retaining a high level of active fluoride and did not attack the inner unlined surface of the aluminum tube.

EXAMPLES 2 – 5

Dental creams are prepared following the standardized development formulation, with the following percentages of the hydrated alumina and of the calcium carbonate (chalk):

| EXAMPLE | 2 | 3 | 4 | 5 |
|---|---|---|---|---|
| hydrated alumina | 46.25% | 46.25% | 26% | 23.75 |
| chalk | 2% | 4% | 20% | 22.50 |

The dental creams containing at least 4% calcium carbonate exhibited a somewhat greater degree of active fluoride during the heat aging test than did the dental cream of Example 2.

The effective range of sodium silicate was determined by testing over the specified range.

Other tests determined that the specified alternate components, e.g., fumed silica in place of sodium silicate and glycerine-sorbitol mixtures in place of glycerine, provide stable dental cream compositions.

The stable dental creams containing more than 5% chalk are formulated with 0.2% sodium tripolyphosphate. Stable dental creams containing 5% chalk have been formulated with and without the sodium tripolyphosphate.

EXAMPLE 6

The following stable dental cream is prepared by standardized development formulation technique:

|  | Parts |
|---|---|
| Glycerine | 22.00 |
| Sodium benzoate | 0.50 |
| Sodium saccharin | 0.20 |
| Sodium carboxymethyl cellulose | 1.50 |
| Sodium silicate | 0.20 |
| Sodium tripolyphosphate | 0.20 |
| Sodium monofluorophosphate | 0.76 |
| Hydrated alumina | 17.60 |
| Calcium carbonate | 17.40 |
| Sodium lauryl sulfate | 1.50 |
| Flavor | 1.00 |
| Water | 0.5 to 100 |

EXAMPLE 7

The following dental cream is prepared:

|  | % |
|---|---|
| glycerine | 6 |
| sorbitol (70%) | 16 |
| sodium benzoate | 0.5 |
| sodium saccharin | 0.2 |
| Irish moss | 1.1 |
| Fumed silica | 1 |
| Water | 24 |
| Hydrated alumina | 47.25 |
| Calcium carbonate | 1 |
| Sodium N-lauroyl sarcosinate | 2.05 |
| Flavor | 0.9 |

This dental cream has a pH of 8.33. Upon being packaged in an unlined aluminum tube, it remains stable upon aging.

It will be apparent to one skilled in the art that various modifications of the foregoing examples may be made thereto.

We claim:

1. A dental cream suitable for compatible incorporation into an unlined aluminum container comprising a dental cream vehicle consisting essentially of as components dispersed or dissolved therein a water-soluble monofluorophosphate salt selected from the group consisting of alkali metal, calcium, magnesium and aluminum monofluorophosphates in an amount which provides between about 0.01% and 1% fluoride to said dental cream, about 35% to 60% by weight of abrasive which abrasive consists essentially of alumina in excess of calcium carbonate, said calcium carbonate being in amount of at least about 2% up to 5% by weight of the total dental cream, and between about 0.05% and 0.25% by weight of a dissolved or dispersed alkali metal silicate or fumed silica; which calcium carbonate and silicate or fumed silica stabilize said dental cream against unlined aluminum container corrosion caused by the presence of said alumina.

2. The dental cream of claim 1 wherein said alumina is hydrated alumina.

3. The dental cream of claim 1 containing between about 40% and 52% of abrasive.

4. The dental cream of claim 3 containing between about 0.15% and 0.25% of said silicate.

5. The dental cream of claim 1 wherein said water-soluble monofluorophosphate is sodium monofluorophosphate and said silicate is sodium silicate.

6. The dental cream of claim 5 wherein said sodium silicate is present in amount between about 0.18% and 0.2% by weight.

7. The dental cream of claim 1 wherein said vehicle comprises between about 20% and 25% by weight of a humectant; between about 0.5% and 5% by weight of a gum; and water.

8. The dental cream of claim 7 wherein said alumina is hydrated alumina, said abrasive is present in amount of between about 40% and 52% by weight, said water-soluble monofluorophosphate is sodium monofluorophosphate, said silicate is sodium silicate and is present in amount between about 0.18% and 0.2%, said humectant contains glycerine, said calcium carbonate is in the form of chalk and said dental cream contains magnesium carbonate in amount up to about 0.5% by weight of said chalk.

9. The dental cream of claim 8 wherein the amount of magnesium carbonate is between about 0.1% and 0.5% by weight of said chalk.

10. A packaged dental cream comprising an unlined aluminum tube and contained therein a dental cream vehicle consisting essentially of as components dissolved or dispersed therein between about 35% and 60% by weight of abrasive, said abrasive consisting essentially of alumina and calcium carbonate, said alumina being present in excess of said calcium carbonate, and said calcium carbonate being in an amount of at least about 2% up to 5% by weight of the dental cream composition; a water-soluble monofluorophosphate salt selected from the group consisting of alkali metal, calcium, magnesium and aluminum monofluorophosphates in an amount which provides between about 0.01% and 1% fluoride in said composition; and between about 0.05% and 0.25% of a dissolved or dispersed alkali metal silicate or fumed silica; which calcium carbonate and silicate or fumed silica stabilize said dental cream against unlined aluminum container corrosion caused by the presence of said alumina.

* * * * *